United States Patent

Hermeling et al.

Patent Number: 5,892,121
Date of Patent: Apr. 6, 1999

[54] PURIFICATION OF TERTIARY PHOSPHINE OXIDES

[75] Inventors: Dieter Hermeling, Böhl-Iggelheim; Randolf Hugo, Dirmstein; Hardo Siegel, Speyer, all of Germany

[73] Assignee: BASF Aktiengesellschaft, Ludwigshafen, Germany

[21] Appl. No.: 968,180

[22] Filed: Nov. 12, 1997

Related U.S. Application Data

[63] Continuation of Ser. No. 702,271, Aug. 23, 1996, abandoned.

[30] Foreign Application Priority Data

Aug. 31, 1995 [DE] Germany .......... 195 32 051.4

[51] Int. Cl.⁶ .......... C07F 9/53
[52] U.S. Cl. .......... 568/14
[58] Field of Search .......... 568/14

[56] References Cited

U.S. PATENT DOCUMENTS

| | | | |
|---|---|---|---|
| 4,675,446 | 6/1987 | Weiss et al. | 568/14 |
| 4,745,224 | 5/1988 | Knebel et al. | 568/14 |
| 5,068,426 | 11/1991 | Telschow | 564/15 |
| 5,292,973 | 3/1994 | Fukumoto et al. | 568/878 |

OTHER PUBLICATIONS

Hadzi, D., Journal of the Chem. Society (Dec., 1962), pp. 5128–5138, "Hydrogen Bonding . . . Part 1".

Thierbach et al, Z. Anorg. Allg. Chem., vol. 477 (1981), pp. 101–107 (English abstract, p. 101).

Primary Examiner—Gary Geist
Assistant Examiner—Sreeni Padmanabhan
Attorney, Agent, or Firm—John H. Shurtleff

[57] ABSTRACT

A process for the purification of tertiary phosphine oxides obtained in a Wittig synthesis as a contaminated by product resulting from the reaction of the corresponding tertiary phosphines, especially triphenylphosphine. The contaminated tertiary phosphine oxides coming from this Wittig synthesis have the formula I

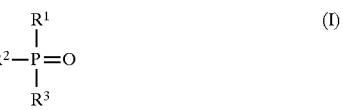

in which $R^1$, $R^2$, and $R^3$ denote $C_1$–$C_{12}$ alkyl, $C_5$–$G_8$ cycloalkyl, aryl, $C_7$–$C_{20}$ aralkyl, or $C_7$–$C_{20}$ alkylaryl. The contaminated phosphine oxide I or phosphine oxide I-containing mixtures, optionally in an inert solvent, are first caused to react with an inorganic or organic acid at temperatures of from 0° to 150° C. to form a crystallized acid salt. The resulting salt crystals are then treated in a purifying step with water or an inorganic base or an organic base to again form the tertiary phosphine oxide. This reformed oxide is then extracted with an inert organic solvent from which the purified tertiary phosphine oxide is finally liberated.

11 Claims, No Drawings

PURIFICATION OF TERTIARY PHOSPHINE OXIDES

This application is a continuation of application Ser. No. 08/702,271, filed Aug. 23, 1996, now abandoned.

The present invention relates to a process for the purification of tertiary phosphine oxides by causing phosphine oxide-containing mixtures to react with an acid and then with water or a base.

Of the tertiary phosphines, triphenylphosphine has the greatest significance due to its use in Wittig syntheses. In this reaction it is converted to triphenylphosphine oxide. Since the need for triphenylphosphine is greater than that for triphenylphosphine oxide, there is no necessity for a separate synthesis of the oxide. It is simpler and cheaper to utilize the triphenylphosphine oxide coming from the Wittig synthesis. Since this triphenylphosphine oxide is contaminated, a purification step is necessary. Theoretically, such purification can take place by distillation. Due to a melting point of 156° to 1° C. and a boiling point of more than 360° C. distillation demands very specialized apparatus which is only rarely available. In addition to distillation, recrystallization is another possible purifying method. With this method, however, usually considerable amounts of the product remain in the mother liquor, and in the case of a high degree of contamination a multiplicity of recrystallizations is necessary. However, in the recovery of triphenylphosphine from triphenylphosphine oxide it is important that the oxide be obtained virtually quantitatively using only a few purification steps.

It is thus an object of the present invention to overcome the above drawbacks and in particular to provide a process involving a minimum of product loss and having a high purifying effect.

Accordingly, we have found a novel and improved process for the purification of tertiary phosphine oxides of the general formula I

in which $R^1$, $R^2$, and $R^3$ denote $C_1-C_{12}$ alkyl, $C_5-C_8$ cycloalkyl, aryl, $C_7-C_{20}$ aralkyl, or $C_7-C_{20}$ alkylaryl, wherein phosphine oxide I or phosphine oxide I-containing mixtures optionally in an inert solvent are caused to react with an inorganic or organic acid at temperatures of from 0° to 150° C. and the resulting salt is then treated with water or an inorganic base or an organic base.

The process of the invention may be carried out as follows:

Phosphine oxide I or phosphine oxide I-containing mixtures can be caused to react with an inorganic or organic acid usually at temperatures of from 0° to 150° C., preferably from 10° to 110° C. and more preferably from 20° to 80° C. in the absence of or, preferably, in the presence of an, eg, added inert solvent and the resulting salt can be separated and then treated with water or an inorganic base or an organic base.

The reaction of tertiary phosphine oxides with acids is described in eg JCS (1962), 5128–5138.

Examples of suitable inorganic acids are mineral acids such as HCl, HBr, HClO$_4$, H$_2$SO$_4$, H$_3$PO$_4$, or Lewis acids such as BF$_3$ or AlCl$_3$, and examples of suitable organic acids are formic acid, acetic acid, and oxalic acid. It is preferable to use cheap acids such as HCl, H$_2$SO$_4$, or H$_3$PO$_4$.

The molar ratio of inorganic or organic acid to the unpurified phosphine oxide I is usually from 0.3:1 to 20:1 and preferably from 0.7:1

If the content of tertiary phosphine oxide 1 in the mixtures of substances cannot be exactly determined, it is advantageous to use an excess of the acid, which is cheaper than the tertiary phosphine oxide, preferably an excess of from 5 to 20 mol %.

Suitable inert solvents are usually those having good dissolving power with respect to the tertiary phosphine oxides 1 and a very poor dissolving power with respect to the salts thereof, such as aromatic hydrocarbons eg benzene, toluene and the xylenes, chlorinated aromatic hydrocarbons eg chlorobenzene, dichlorobenzene, aliphatic hydrocarbons such as n-pentane, mixtures of pentane isomers, n-hexane, mixtures of hexane isomers, n-heptane, mixtures of heptane isomers, octane, and mixtures of octane isomers, cycloaliphatic hydrocarbons such as cyclopentane, cyclohexane, cycloheptane, and cyclooctane or aromatic nitrites such as benzonitrile.

The separation of the salts can take place following crystallization to completeness, for example by physical separating methods, preferably by filtration or centrifugation.

Depending on the degree of purity required the separated salt can be washed once or a number of times. Preferably, washing is effected using the said inert solvent used. The salt can be dried, but is usually caused to react further in the solvent-moist state. The free tertiary phosphine oxide 1 can be obtained from the salts eg by treatment with an inorganic base or an organic base, preferably an aqueous alkaline solution or a base-reacting compound, eg, hydroxides, carbonates, formamides, acetates, and C$_1$–C$_8$ alkylamines such as NaOH, KOH, Ca(OH)$_2$, Na$_2$CO$_3$, NaHCO$_3$, Na$_2$S, NH$_3$, sodium form ate, sodium acetate, potassium form ate, potassium acetate, methylamine, triethylamine, and aniline, preferably NaOH, KOH, Na$_2$CO$_3$, NH$_3$, and triethylamine, more preferably NaOH, NH$_3$, and triethylamine and most preferably by treatment with water.

The purified tertiary phosphine oxide 1 can be obtained for example by extraction with an inert solvent by generally known methods. Theoretically, the acid can be subsequently recovered from the aqueous solution by concentration and purification.

The liberation of the tertiary phosphine oxides 1 from salts thereof may also take place thermally. It is advantageous to combine the thermal dissociation with a distillation. It is of no significance whether the tertiary phosphine oxide or the acid or Lewis acid is the more readily volatile component.

The substituents $R^1$, $R^2$, and $R^3$ in the compounds I may be different from each other or are, preferably, all identical, and have the following meanings:

$C_1-C_{12}$ alkyl, preferably $C_1-C_8$ alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl and more preferably $C_1-C_4$ alkyl such as methyl, ethyl, n-propyl, isopropyl, n-butyl, isobutyl, sec-butyl, and tert-butyl, $C_5-C_8$ cycloalkyl such as cyclopentyl, cyclohexyl, cycloheptyl, and cyclooctyl, preferably cyclopentyl, cyclohexyl, and cyclooctyl and more preferably cyclopentyl and cyclohexyl, aryl such as phenyl, 1-naphthyl, 2-naphthyl, 1-anthryl, 2-anthryl and 9-anthryl, preferably phenyl, 1-naphthyl and 2-naphthyl and more preferably phenyl, $C_7-C_{20}$ aralkyl, preferably $C_7-C_{12}$ phenylalkyl such as benzyl, 1-phenethyl, 2-phenethyl, 1-phenyl propyl, 2-phenyl propyl, 3-phenyl propyl, 1-phenyl butyl, 2-phenylbutyl, 3-phenylbutyl and 4-phenylbutyl and more preferably benzyl, 1-phenethyl and 2-phenethyl, $C_7$–$C_{20}$ alkylaryl, preferably $C_7$–$C_{12}$ alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphen-yl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphen-yl, and 4-n-propylphenyl.

Preferred tertiary phosphine oxides of the general formula I are:

Trimethylphosphine oxide, triethylphosphine oxide, tributylphosphine oxide, tri hexylphosphine oxide, trioctylphosphine oxide, tricyclohexylphosphine oxide, triphenylphosphine oxide, tritolylphosphine oxide, dimethylbutylphosphine oxide, dimethylhexylphosphine oxide, dimethyloctylphosphine oxide, dibutylmethylphosphine oxide, dibutylhexylphosphine oxide, dibutyloctylphosphine oxide, dihexylmethylphosphine oxide, dihexylbutylphosphine oxide, dihexyloctylphosphine oxide, dioctylmethylphosphineoxide, dioctylbutylphosphine oxide, dioctylhexylphosphine oxide, ditolylphenylphosphine oxide, diphenyltolylphosphine oxide, or mixtures thereof.

Tertiary phosphine oxides such as triphenylphosphine oxide are used as flame retardants in plastics materials (U.S. Pat. No. 4,278,588) or as catalysts for reactions involving phosgene (U.S. Pat No. DE 3,019,526). Furthermore, tertiary phosphines such as triphenylphosphine can be recovered from their oxides (O.Z. 44,237).

EXAMPLES

Example 1

To a solution of 375 g (1.35 mol) of triphenylphosphine oxide in 2,625 g of chlorobenzene there were added, dropwise over a period of 30 minutes, 135 g (1.35 mol) of 98% strength $H_2SO_4$ and stirring was continued for 30 minutes.

The crystals were filtered off, washed three times with 500 mL of chlorobenzene each time and dried. There were obtained 500.6 g (1.33 mol) of triphenylphosphine oxide/sulfuric acid adduct.

To 200 g (0.531 mol) of the triphenylphosphine oxide/sulfuric acid adduct in 1500 mL of chlorobenzene there were stirred in 1500 mL of water over a period of one hour. Following phase separation, the aqueous phase was extracted three times with 500 mL of chlorobenzene each time. Following the removal of the solvent there were obtained 146 g (97.5%) of triphenylphosphine oxide.

Example 2

To a solution of 46.9 g of triphenylphosphine oxide (ca 70% strength) in 230 mL of chlorobenzene there were added, dropwise over a period of 10 minutes, 6.9 g of 98% strength sulfuric acid. The purification was carried out in a manner similar to that described in Example 1 and there were obtained 38.3 g of triphenylphosphine oxide/sulfuric acid adduct and, from this, 27.9 g of triphenylphosphine oxide (based on 70% starting product this points to a refind rate of 85%).

Example 3

To 25 g of distillation residues containing ca 50% of triphenylphosphine oxide in 75 mL of chlorobenzene there were added, dropwise at room temperature, 2.3 g of $H_2SO_4$ (98%) and stirring was continued over a period of 1.5 hours. The crystals were filtered off in vacuo, washed twice with 50 mL of chlorobenzene and dried. There were obtained 14 g of triphenylphosphine oxide/sulfuric acid adduct. The triphenylphosphine oxide was subsequently isolated as described in Example 1. There were obtained 10.2 g of triphenylphosphine oxide.

Example 4

To 20 g (72 mmol) of triphenylphosphine oxide in 50 mL of chlorobenzene there were added 3.3g (37 mmol) of oxalic acid and the mixture was heated to 120° C. Following cooling, the triphenylphosphine oxide/oxalic acid adduct was filtered off in vacuo, washed with 50 mL of chlorobenzene and dried. There were obtained 12.9 g (96%) of a 1:1 adduct of triphenylphosphine oxide and oxalic acid, mp 105°–110° C.

The $[Ph_3PoH]^+[HOOC—COO]^-$ was suspended in 100 mL of chlorobenzene and 100 mL of saturated $NaHCO_3$ solution were added. Following phase separation, the aqueous phase was extracted twice with 50 mL of chlorobenzene each time and the organic phase was isolated from the solvent. There were obtained 9.5 g (34 mmol) of triphenylphosphine oxide.

We claim:

1. In a process for the purification of a tertiary phosphine oxide or mixtures thereof of the formula I

wherein each of $R^1$ $R^2$ and $R^3$ denotes $C_1$–$C_{12}$-alkyl, $C_5$–$C_8$-cycloalkyl, aryl, $C_7$–$C_{20}$-aralkyl or $C_7$–$C_{20}$-alkylaryl,
  coming from a Wittig synthesis in contaminated form, the improvement which comprises:
    first reacting said contaminated phosphine oxide I or its mixtures with an inorganic or organic acid, optionally in an inert solvent which preferentially dissolves said phosphine oxide but not its salts, at temperatures of from 0° to 150° C. to form a crystallized salt of said acid, separating the resulting crystallized acid salt from the reaction mixture followed subsequently by a purifying treatment of said separated crystallized acid salt with water or an inorganic base or an organic base, extracting the tertiary phosphine oxide formed with said inert solvent, and only then liberating the purified tertiary phosphine oxide from its preferential solvent.

2. A process for the purification of tertiary phosphine oxides I as defined in claim 1, wherein the inorganic acid used is a mineral acid or a Lewis acid.

3. A process for the purification of tertiary phosphine oxides defined in claim 1, wherein the first reaction is carried out in said preferential inert solvent.

4. A process for the purification of tertiary phosphine oxides 1 as defined in claim 1, wherein the inert solvent used is an aromatic hydrocarbon, a chlorinated aromatic hydrocarbon, an aliphatic hydrocarbon, a cycloaliphatic hydrocarbon, or an aromatic nitrile.

5. A process for the purification of tertiary phosphine oxides I as defined in claim 1, wherein $R^1$, $R^2$, $R^3$ are phenyl groups.

6. A process for the purification of tertiary phosphine oxides I as defined in claim 1, wherein sulfuric acid is used as inorganic acid.

7. A process for the purification of tertiary phosphine oxides I as defined in claim 1, wherein oxalic acid is used as organic acid.

8. A process as claimed in claim 1, wherein the inert solvent used is chlorobenzene.

9. A process as claimed in claim 1, wherein the purified tertiary phosphine oxide is liberated by extraction with an inert solvent.

10. A process as claimed in claim 1, wherein the purified tertiary phosphine oxide is liberated by thermal dissociation.

11. A process as claimed in claim 10, wherein said thermal dissociation is combined with a distillation to liberate the purified product.

* * * * *